United States Patent [19]

Hlavinka et al.

[11] 4,399,030

[45] Aug. 16, 1983

[54] RINSING, CLEANING AND DISINFECTING DIALYSATE PREPARATION AND SUPPLY APPARATUS

[75] Inventors: Dennis J. Hlavinka; Steven H. Johnson, both of Lakewood; James L. Zook, Denver, all of Colo.

[73] Assignee: Cobe Laboratories, Inc., Lakewood, Colo.

[21] Appl. No.: 258,424

[22] Filed: Apr. 28, 1981

[51] Int. Cl.³ .................................................. B01D 31/00
[52] U.S. Cl. ..................................... 210/91; 210/140; 210/321.3
[58] Field of Search ................. 210/321.3, 96.2, 140, 210/91; 128/DIG. 24; 422/1.36; 134/22.11, 22.12, 22.14, 113, 171, 57 R

[56] References Cited

U.S. PATENT DOCUMENTS

| | | | |
|---|---|---|---|
| 3,170,667 | 2/1965 | Szohatzky | 251/149.6 |
| 3,871,913 | 3/1975 | Shaldon | 134/22.11 X |
| 4,150,673 | 4/1979 | Watt | 128/DIG. 24 X |
| 4,166,031 | 8/1979 | Hardy | 210/96.2 X |
| 4,209,402 | 6/1980 | Gentles | 210/140 X |
| 4,332,264 | 6/1982 | Gortz et al. | 210/140 X |

Primary Examiner—Frank A. Spear, Jr.

[57] ABSTRACT

A cleaning and/or disinfecting system for flushing water and chemical treatment liquids through the hydraulic circuitry of dialysate preparation and supply apparatus, the system employing, for each particular treatment liquid of a plurality of possible liquids, a keyhole adjacent to a chemical intake port and means to send electrical signals to an electrical controller indicating the presence of a key within a particular keyhole, whereby the particular treatment liquid connected to the port is flushed through the hydraulic circuitry of the apparatus at the proper flowrate and for the desired period of time.

6 Claims, 12 Drawing Figures

BLEACH MODE

AUTOMATIC ULTRAFILTRATION CONTROL MODE

MANUAL RINSE MODE

RINSING, CLEANING AND DISINFECTING DIALYSATE PREPARATION AND SUPPLY APPARATUS

FIELD OF THE INVENTION

The invention relates to cleaning and/or disinfecting systems for dialysate preparation and supply apparatus.

BACKGROUND OF THE INVENTION

Dialysate is typically continuously prepared by mixing a concentrated solution and water in apparatus containing a number of pumps, chambers, valves and flow restrictors in its hydraulic circuitry. It is often desirable to remove the source of concentrated solution and flush the hydraulic circuitry with water or treatment chemicals such as a cleanser or a bleach between uses, and it is desirable to have different treatment chemicals within the circuitry for different periods of time and pumped through it at different concentrations.

SUMMARY OF THE INVENTION

It has been discovered that operator usage can be simplified, and apparatus cleaning and/or disinfecting made more reliable, by providing, for each different liquid to be used, a keyhole adjacent to the chemical intake port and means to send electrical signals to an electrical controller indicating the presence of a key within the particular keyhole. The key attached to a connector for one liquid will not fit into a keyhole for another liquid; thus the particular treatment liquid connected to the port is flushed through the hydraulic circuitry at the proper concentration and for the desired period of time.

In preferred embodiments the connectors and key holes are color-coded to further simplify operator usage; one of the treatment liquids is a disinfectant (most preferably formaldehyde), and the controller causes the disinfectant to soak in the machine for a period of time; and one of the treatment liquids is a bleach cleanser.

PREFERRED EMBODIMENT

The structure and operation of the presently preferred embodiment of the invention will now be described, after first briefly describing the drawings.

DRAWINGS

STRUCTURE

Figure 1:
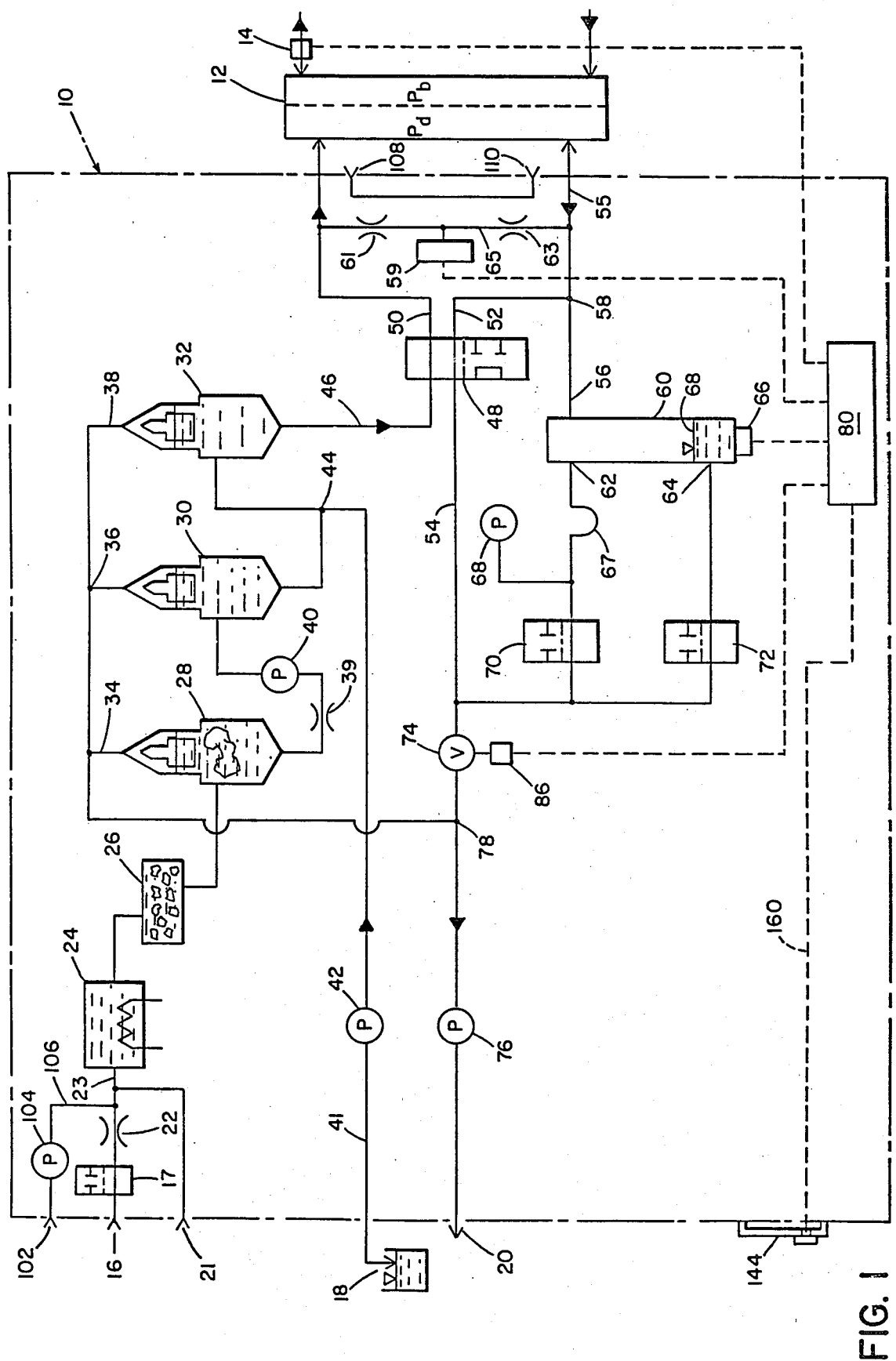
FIG. 1 is a diagrammatic representation of a dialysate preparation supply and control system according to the invention.

Referring to FIG. 1, there is shown a dialysate preparation, supply and control system 10 connected to externally located dialyzer 12, venous blood pressure transducer 14, and dialysate concentrate source 18. Port 16 is for external connection to a source of water, and port 20 is for draining used dialysate. Inside system 10 port 16 is connected to water inlet valve 17, which is normally open to allow flow of water through the machine, whenever the machine is turned on. Valve 17 is connected to flow control restrictor 22, which only allows approximately 600 cc/min flow, and this is connected by line 23 to 1200 watt heater 24, which heats water to approximately 38.0° C. via a temperature control circuit of a type well known in the art. Rinse port 21 is connected to the flow line 23. Heater 24 is connected to nucleation chamber 26, containing chopped polypropylene netting (pieces less than approximately ⅛ inch in size, sold under Vexar trademark) between two filters in the chamber, and chamber 26 is connected in series to deaeration chambers 28 and 30, and air-bypass/stabilizer chamber 32. Chamber 28 contains crumpled polypropylene netting. Gas separated from the liquid in the deaeration chambers, and gas that may have been admitted via the concentrate inlet line 41, is removed via lines 34, 36, 38, and the deaerated liquid is removed from the bottoms of the chambers. Flow restriction orifice 39 and positive displacement pump 40 are located between the liquid outlet of chamber 28 and the liquid inlet of chamber 30. Concentrated dialysate solution from source 18 is pumped through line 41 by pump 42 and mixes with deaerated water at junction 44 between deaeration chamber 30 and air-bypass/stabilizer chamber 32.

The liquid outlet of chamber 32 is connected by line 46 to two-position, four-connection valve 48. The other lines connected to valve 48 are dialyzer supply line 50, dialyzer return line 52 and dialysate drain line 54. In FIG. 1 valve 48 is shown in a dialysate supply mode with dialysate line 46 connected to supply line 50, and dialysate return line 52 connected to drain line 54. In the bypass mode the lines are connected to the flow paths indicated in the bottom half of the schematic representation of valve 48. Thus, in the bypass mode, line 46 is connected directly to line 54, and lines 50 and 52 are blocked, thereby forcing any liquid flowing out of the dialyzer through line 55 to go through line 56 connected to the dialysate return line 52 and line 55 at junction 58. Dialysate pressure in the membrane device 12, $P_d$, is sensed by pressure transducer 59, which is connected to hydraulically average the dialysate pressure immediately before entering dialyzer 12 and immediately after exiting from dialyzer 12. Averaging of the dialysate pressure is accomplished via orifices 61 and 63, which permit fluid to flow through line 65 at a rate which is small in comparison to the flow through the dialyzer. Pressure transducer 59 is connected to line 65 midway between orifices 61 and 63.

Line 56 is connected to ultrafiltrate collection tube 60, which has air inlet 62, drain 64, and sonic transmitter/receiver 66, which sonically measures the height of the upper surface 68 of the dialysate within tube 60. Tube 60 is approximately 7" in height and has an inner diameter of 0.531". Air inlet 62 is connected via surge loop 67 to air pump 68 and to two-position valve 70, shown in its open position in FIG. 1. Dialysate drain 64 is connected through two-position valve 72 to dialysate drain line 54. (In FIG. 1 valve 72 is also shown in the open position.) Dialysate drain line 54 is connected to variable restriction valve 74 (described in more detail below and in FIGS. 2 and 3), pump 76 and drain port 20. Pump 76 and pump 40 have a common motor and drive shaft, resulting in the same flow of fluid through each. The air from deaeration chambers 28 and 30, and from air-bypass/stabilizer chamber 32, joins with the used dialysate at junction 78, located upstream of pump 76, and is also pumped to drain 20 with the used dialysate. Controller 80, the operation of which is described in detail below, is connected to receive electrical signals (the dotted lines on FIG. 1 indicating electrical paths) from venous blood pressure transducer 14, dialysate pressure transducer 59, sonic transmitter/receiver 66 and ultrafiltration display and control panel 144, and to send electrical signals to panel 144 and motor 86, the opening and closing mechanism for variable restriction valve 74.

Figure 2:
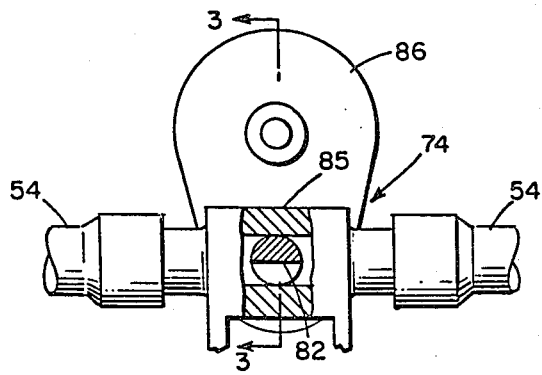
FIG. 2 is an elevation, partially broken away, of a variable restriction valve used in the FIG. 1 system.
Figure 3:
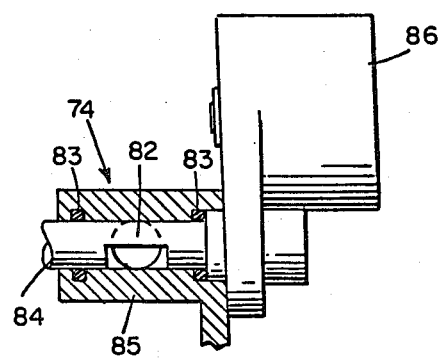
FIG. 3 is a side elevation, partially broken away, of the FIG. 2 device.

Referring to FIGS. 2 and 3, variable restriction valve 74 is shown with its control mechanism. Valve 74 includes hemicylindrical obstructor 82, which is a portion of shaft 84 positioned in the flow path of line 54. Elastomeric O-rings 83 provide a seal between the shaft 84 and the interior surface of a cylindrical cavity in housing 85. Rotation of shaft 84 about its longitudinal axis on an axis transverse to the direction of flow in line 54 is caused by stepper motor 86, which is controlled by controller 80, has a step angle of 0.125° and is available from North American Philips Control Corp., Chesire, Conn. as part No. K 82237. With obstructor 82 in the position shown in FIG. 2, the valve is open. As obstructor 82 is rotated about the axis of shaft 84 from this open position, it blocks more of the flow passage.

Figure 4:
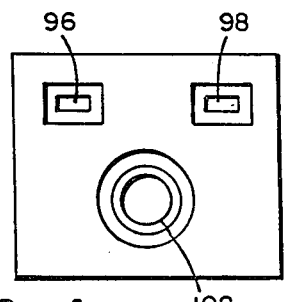
FIG. 4 is an elevation of an external fluid port for the FIG. 1 system.
Figure 5:
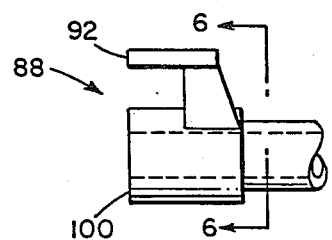
FIG. 5 is a side elevation of an external fluid connector.
Figure 6:
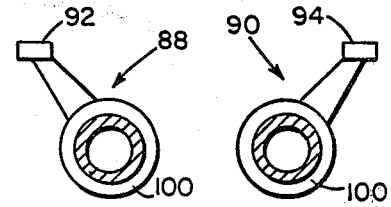
FIG. 6 is a vertical sectional view, taken at 6—6 of FIG. 5, of external fluid connectors.

Referring to FIGS. 4-6, there are shown the external connections for bottles (not shown) of the cleaning and disinfectant treatment liquid solutions. Formaldehyde disinfectant connector 88 and bleach connector 90 have keys 92, 94 for mating with keyholes 96, 98, respectively, when the associated tubular portion 100 is inserted into port 102 on a panel of the dialysate machine. Keys 92, 94 activate infrared optical switches 112, 114 (shown in FIG. 7) upon insertion and activate the proper cleaning cycle. The bottle and key connector and the lip around the keyhole for each solution also have a matching color which is different from the color for connector and lip of the other solution to further simplify operator usage.

Figure 8:
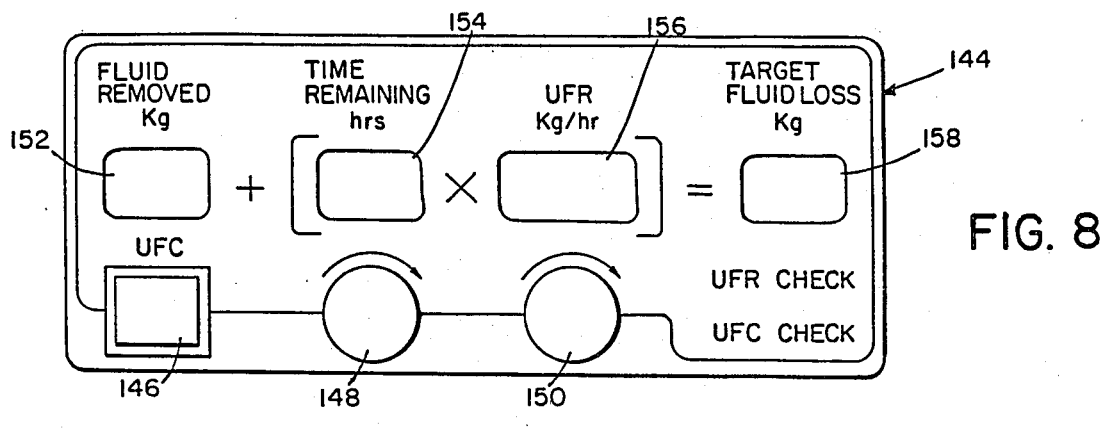
FIG. 8 is a plan view of a display and control panel of the FIG. 1 system.
Figure 11:
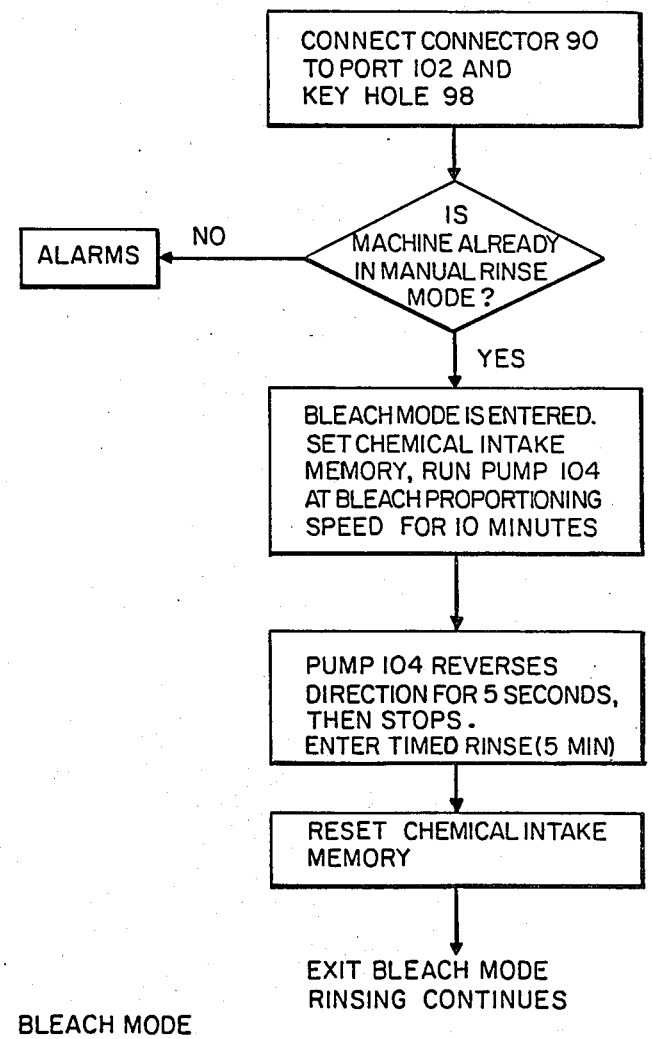
FIGS. 10–12 are flow diagrams describing methods of rinsing, cleaning, and disinfecting the FIG. 1 system.

Referring to FIG. 8, there is shown the ultrafiltration display and control panel 144 attached to the face of the housing enclosing system 10. It has push button 146 (to begin the automatic ultrafiltration control (UFC) mode), time control knob 148 (to enter the total time to be under the UFC mode, generally a few minutes less than the time for the entire dialysis session), ultrafiltration rate control knob 150 (to enter the initial desired ultrafiltration rate), and digital displays 152, 154, 156, 158, for presenting the fluid removed, the time remaining in the UFC mode, the current ultrafiltration rate, and the target fluid loss respectively. The push button, knobs, and displays are all electrically connected to controller 80 by line 160 (FIG. 1). The display panel presents an equation for ultrafiltration with displays 152, 154, 156, 158 taking the places of the variables. The equation is that the fluid removed plus the product of the time remaining times the ultrafiltration rate equals the target fluid loss.

Figure 7:
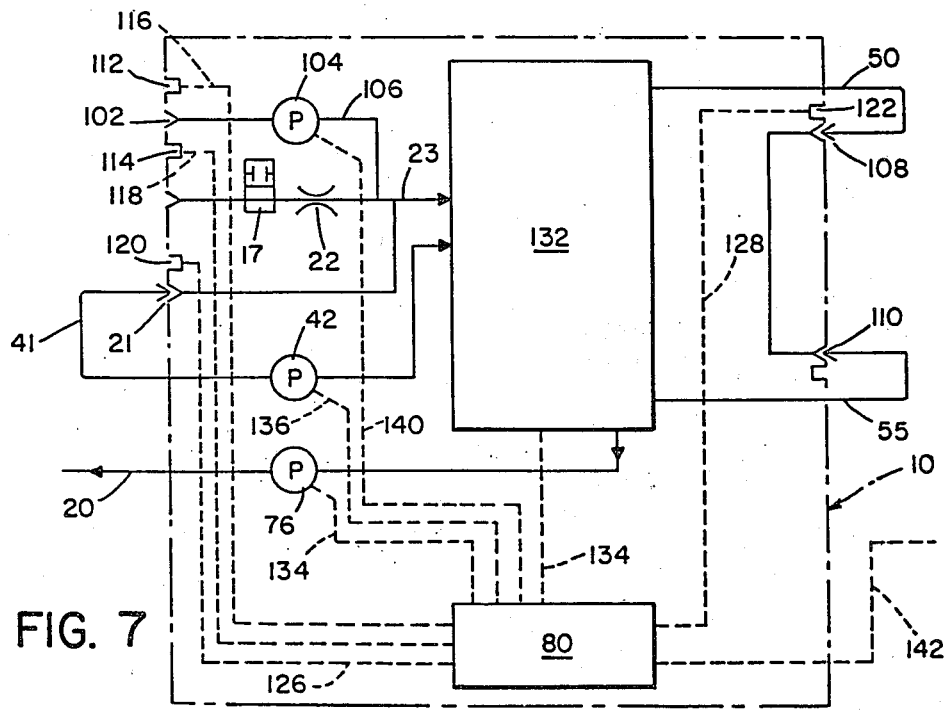
FIG. 7 is a diagrammatic representation of a cleaning, disinfecting, and rinsing subsystem of the FIG. 1 system.

Referring to FIG. 1 and to FIG. 7 (showing the cleaning and disinfecting subsystem components), it is seen that port 102 is connected through chemical pump 104 and line 106 to the line 23 between flow control restrictor 22 and heater 24. Also, ports 108, 110 are internally connected to each other to provide a short-circuit path for dialysate lines 50, 55 during cleaning, disinfecting, and rinsing procedures.

Referring to FIG. 7, there are shown optical paths 112, 114, that each are interrupted when key 92 or 94 is inserted in its respective keyhole 96 or 98. The senders and receivers for optical paths 112, 114 are connected to controller 80 by electrical paths 116, 118, respectively, and the interruption of the optical paths indicates to controller 80 which chemical solution is connected to port 102, and which cycle is to be activated.

Proximity switches 120, 122 are connected to controller 80 by electrical paths 126, 128 and are closed when hoses 41 and 50 or 55 are connected to ports 21, 108 respectively. Pumps 40 (within hydraulic flowpaths generally indicated 132 in FIG. 7), 42, 76, 104 are connected to controller 80 by electrical paths 134, 136, 134, 140, respectively. (Pumps 40 and 76 are driven by the same motor.) Electrical path 142 is connected to controller 80 to indicate whether a blood pump (not shown) is operating.

OPERATION

The interaction of the different components represented in FIGS. 1-8 will be discussed on a subsystem by subsystem basis.

Deaeration Subsystem

The water is deaerated prior to mixing with the concentrated dialysate solution at junction 44 by subjecting it to low pressure through the actions of positive displacement pump 40, which is attempting to pump at approximately 1000 cc/min, and flow control restrictor 22, which only allows approximately 600 cc/min flow. (Four hundred cc/min of fluid flow through pump 40 is water vapor, which converts back to the liquid phase downstream.) Also, the temperature of the water is raised by heater 24 to reduce gas solubility. The heated, low-pressure water flows downward in nucleation chamber 26 over the chopped polypropylene, which provides sites at which the air bubbles form and grow. From there the water and bubbles pass into deaeration chamber 28, where large bubbles immediately rise and small bubbles increase in size on the crumpled polypropylene. The bubbles rise to the water surface and exit from chamber 28 via line 34, and the deaerated water is pumped out of the bottom. The air removed from this chamber is pumped to drain port 20 by pump 76, which acts as a low pressure sink. Most of the dissolved air is removed from the incoming water in chamber 28, and by removing it before the water passes through pump 40, the vacuum formation and deaeration are improved. Deaeration chamber 28 is held at pressure slightly higher (50 to 100 mm Hg) than the intake of pump 40 by flow restrictor 39 in order to move the air to pump 76, the intake of which operates at a pressure below the pressure upstream from restrictor 39. If this increase in pressure were not used, the air and liquid would both flow through pump 40 along the path of lowest pressure. (The intake of pumps 40 and 76 are nominally at the same pressure, the vapor pressure of water.) A small amount of further degassing occurs between flow restrictor 39 and pump 40, and deaeration chamber 30 is used to remove any additional gas pulled from the flowing water. Again, air is removed through outlet line 36 and pumped to the drain by pump 76. Air bypass/stabilizer chamber 32 is used to remove any air bubbles that enter the hydraulic pathway via the dialysate concentrate flowstream. This chamber also provides a stabilizing site at which short term dialysate temperature and conductivity variations average out.

Ultrafiltration Rate Measurement Subsystem

Periodically throughout a dialysis session, the rate of ultrafiltration (i.e., the net flow of liquid from the blood side of the membrane in dialyzer 12 to the dialysate side) is measured. If the dialysate pressure, $P_d$, is more negative than $-165$ mm Hg, prior to making the ultrafiltration measurement, $P_d$ is adjusted to a more positive value by adjusting valve 74. This is to avoid degassing which occurs at these low pressures, and which would otherwise displace liquid and incorrectly increase the measured amount of liquid flowing into collection tube 60. System 10 first goes into a bypass mode by moving valve 48 into the position connecting the flow circuits represented on the bottom half of the symbol in FIG. 1. Thus, lines 46 and 54 are connected to each other in a short circuit, and lines 50 and 52 are blocked, causing a flow equal in amount to the ultrafiltrate (i.e., the liquid passing through the membrane) to flow through tube 56 and into collection tube 60, where it can be measured. The liquid is initially purged from tube 60 by placing valve 70 in the blocked position and valve 72 in the open position and activating air pump 68, resulting in pumping most of the dialysate within tube 60 out of exit 64. The air pump is then deactivated, and the machine waits for 15 seconds for pressure perturbations in the hydraulic system to die out. During this waiting interval, the ultrafiltrate that comes into the collection tube via line 56 passes out through exit 64 and valve 72. At the end of the interval, valve 70 opens and valve 72 closes, and the ultrafiltrate entering tube 60 will then be captured. The tube gradually fills with ultrafiltrate, the displaced air from tube 60 passing through valve 70 to the drain 20. The rate at which the tube fills is the ultrafiltration rate. The increasing height 68 of liquid in tube 60 is measured every two seconds by sonic transmitter/receiver 66. At the end of 60 seconds, there are 31 data points, and controller 80 applies a least squares regression, by well-known techniques, to determine the average ultrafiltration rate for the 60-second interval. After the measurement has been made, valve 48 moves to the dialyze position, and valves 70 and 72 are kept in the open positions to allow for continuous flushing of the measurement apparatus.

When ultrafiltrate collection begins, the line between valve 70 and port 62 is normally filled with air. Pressure perturbations in line 54 during collection could force fluid into the collector through port 62, were it not for the presence of surge loop 67.

The filling of collection tube 60 allows for accurate measurement of the very low flowrates involved with ultrafiltration, and the averaging of the large number of data points avoids distortion of the measurement by short-term variations caused, e.g., by an increase in blood pressure owing to movement of the patient during the measurement. Moreover, this system accurately measures a wide range of flow rate values, and can be made to measure an even wider range by having the tube tapered.

Transmembrane Pressure and Ultrafiltration Control Subsystem

The transmembrane pressure (TMP) of dialyzer 12 is the difference between the blood pressure, $P_b$, sensed by transducer 14, and average dialysate pressure, $P_d$, sensed by transducer 59. ($P_b$ is sensed at the outlet; in calculating TMP, 15 mm Hg is added to the sensed value to approximate an average "mid-line" $P_b$.) The rate of ultrafiltration (UFR) across the membrane in dialyzer 12 is dependent upon the TMP, and can be controlled by controlling the TMP. These relationships are described by equations 1 and 2:

$$TMP = P_b - P_d \tag{1}$$

$$UFR = f(TMP) \tag{2}$$

Because $P_b$ cannot be controlled by machine 10, the TMP and the ultrafiltration rate are controlled by adjusting $P_d$. Regardless of position of valve 48, $P_d$ is controlled by upstream pump 40, downstream pump 76 and variable flow restriction valve 74. Pump 40 pushes fresh dialysate toward the dialyzer, and pump 76 pulls used dialysate from it. If valve 74 is completely open, pump 76 dominates, and its low inlet pressure causes $P_d$ to be approximately $-400$ mm Hg. As valve 74 obstructs more and more of the flow passage, pump 40 becomes more dominant, pushing liquid to dialyzer 12 at increased pressure up to approximately $+200$ mm Hg. Attaining the positive pressure permits achieving very low TMP's when, e.g., a very low rate of ultrafiltration is desired, perhaps in response to the symptoms of particular patients, or when the blood pressure in the dialyzer is quite high. The particular structure of variable restriction valve 74 is particularly advantageous in changing $P_d$, because the change in occlusion for a given step (i.e., angular change) of the obstructor decreases as total occlusion is approached, and the relationship between $P_d$ and rotation of shaft 84 is approximately linear over most of the desired range of dialysate pressure. Thus, each step of motor 86 results in approximately the same increase or decrease in $P_d$.

In the automatic ultrafiltration control (UFC) mode of operation of system 10, a predetermined amount of liquid is automatically removed from the patient during the dialysis session. Controller 80 periodically monitors the ultrafiltration rate (UFR), via the UFR measuring subsystem described above, and adjusts the TMP accordingly by varying $P_d$ with valve 74, so that the total amount of fluid to be removed from the patient is smoothly drawn across the dialyzer membrane during the dialysis period.

Figure 9:
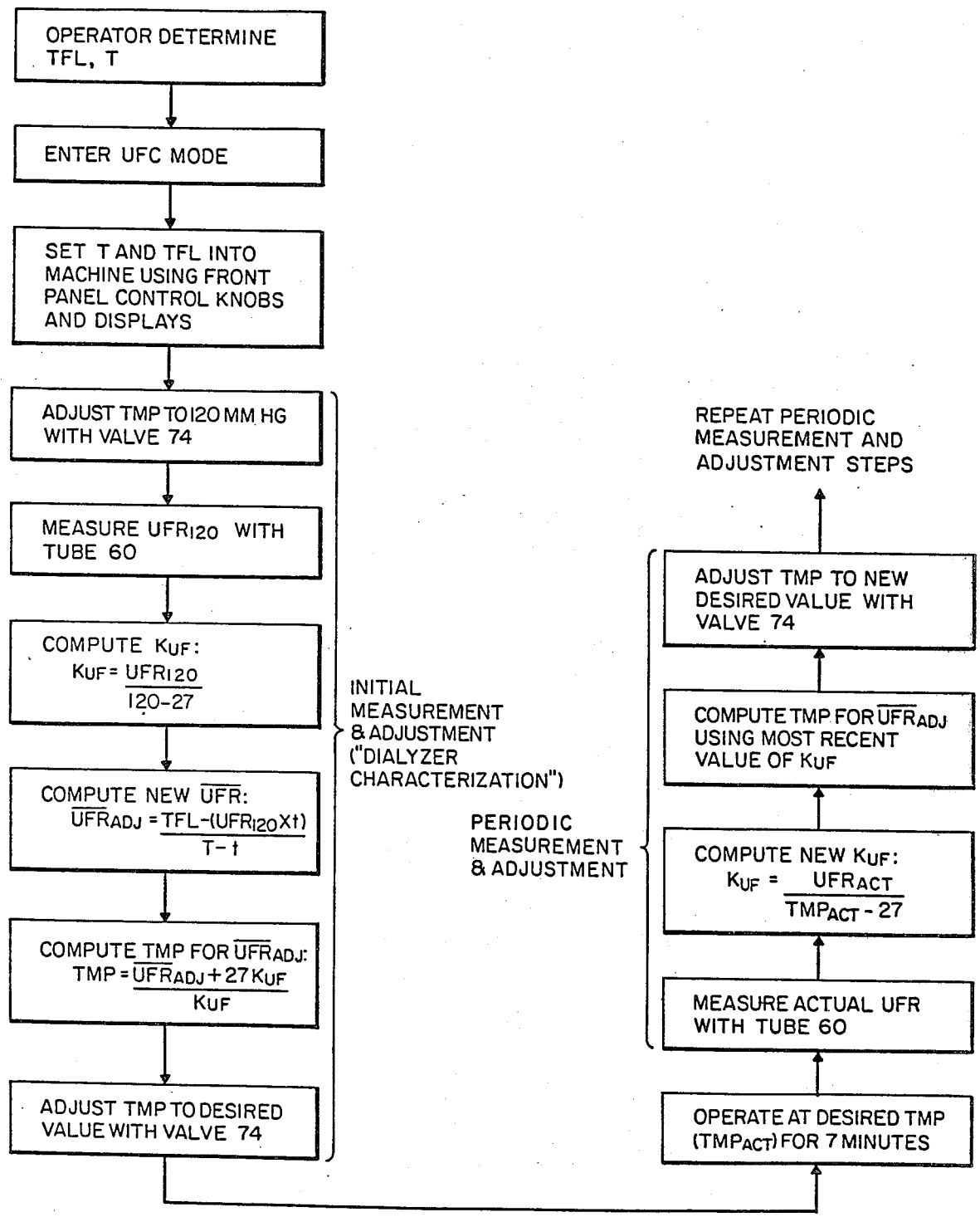
FIG. 9 is a flow diagram describing a method of controlling ultrafiltration in the FIG. 1 system.
Figure 10:
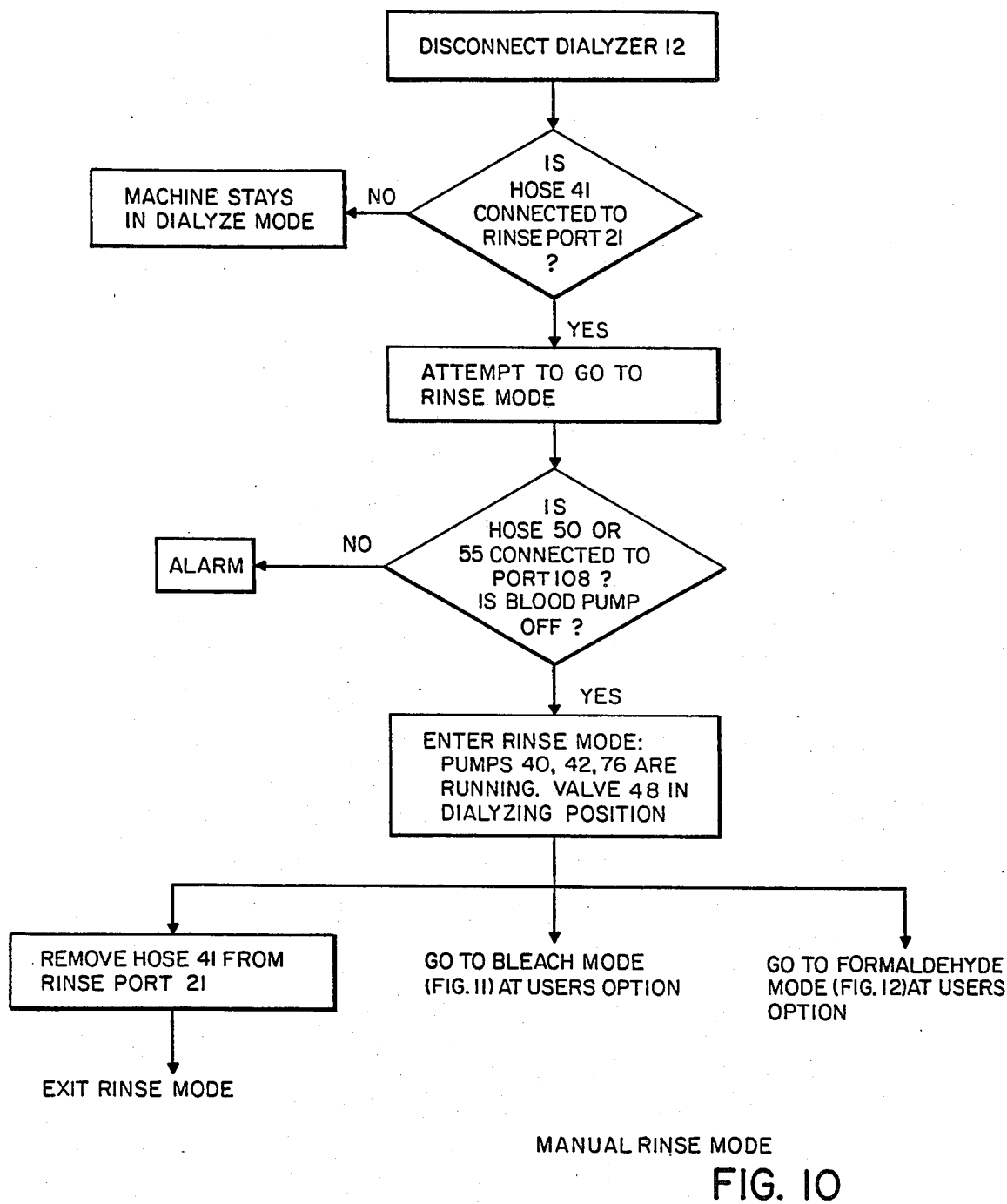
Figure 12:
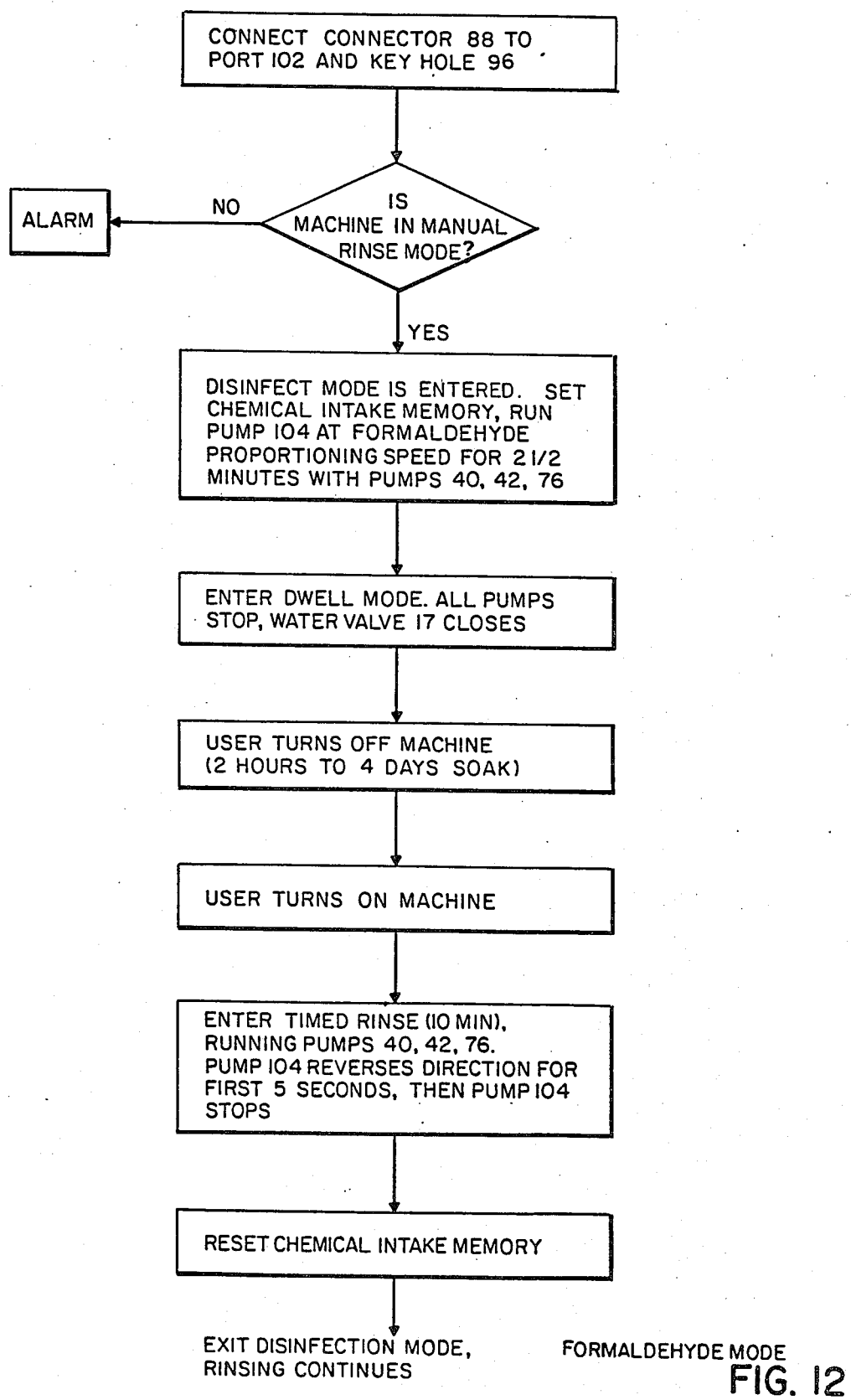

Referring to FIGS. 8 and 9, at the beginning of a dialysis session the user enters the automatic mode by pushing button 146, and determines the desired amount of fluid to be removed from the patient, i.e., target fluid loss (TFL), and the overall time for the dialysis session (T). The time is entered by turning knob 148 until the time appears in display 154. The target fluid loss is entered by turning the UFR knob 150 until the desired TFL appears in display 158. The average rate of ultrafiltration, $\overline{UFR}$, to result in this amount of liquid removal, i.e., TFL, by the end of the overall period is given by equation 3.

$$\overline{UFR} = TFL/T \qquad (3)$$

Because users are interested in total liquid loss, including that owing to perspiration and exhalation, in determining the $\overline{UFR}$ actually used in the machine, 30 gm/hr, the average adult moisture loss by perspiration and exhalation, is subtracted from $\overline{UFR}$.

Initially, valve 74 is adjusted by controller 80 to create a TMP of approximately 120 mm Hg, and after maintaining that TMP for a short period of time, the UFR associated with that TMP (UFR$_{120}$) is measured as described above by controller 80 with system 10 in the bypass mode. This is known as a "dialyzer characterization" measurement. System 10 is then returned to the dialysate supply mode. The construction of system 10 and controller 80 is such that the desired TMP can be maintained within the dialyzer 12 whether valve 48 is in the dialysate supply mode or the bypass mode.

The relationship between UFR and TMP for dialyzer 12 is determined by equation 4, which assumes that a linear function is followed, and that the UFR will be zero at a TMP of approximately 27 mm Hg, the oncotic pressure. ("Oncotic pressure", often referred to as "colloid osmotic pressure" or "protein osmotic pressure", acts in a direction opposite to TMP and is caused by the presence of blood and dialysate on opposite sides of a membrane.)

$$UFR = K_{UF}(TMP-27) \qquad (4)$$

where: $K_{UF}$ is the UF coefficient of dialyzer 12.

$K_{UF}$ is computed by equation 5, knowing the ultrafiltration rate achieved at the 120 mm Hg TMP:

$$K_{UF} = UFR_{120}/(120-27) \qquad (5)$$

An adjustment to $\overline{UFR}$ (resulting in $\overline{UFR}_{adj}$) presented in equation 6 is made to account for the fact that the system probably does not operate at $\overline{UFR}$ during the initial 120 mm Hg TMP dialyzer characterization measurement:

$$\overline{UFR}_{adj} = \frac{TFL - (UFR_{120} \times t)}{T-t} \qquad (6)$$

where: t is the elapsed time from the beginning of ultrafiltration control mode. For example, if a very high UFR is desired, too little fluid will be removed during dialysis at the dialyzer characterization TMP setting.

The TMP necessary to achieve $\overline{UFR}_{adj}$ is then computed using equation 7:

$$TMP = (\overline{UFR}_{adj} + 27\, K_{UF})/K_{UF} \qquad (7)$$

After making the computations described above, controller 80 sends electrical signals to valve 74 to adjust the TMP to the value computed using equation 7. A feedback control subsystem within system 10 will thereafter keep the measured value of TMP, via sensors 14 and 59, coincident with the desired value from equation 7. Approximately seven minutes after this first UFR measurement and TMP adjustment, a second UFR measurement is made (the UFR ideally is $\overline{UFR}_{adj}$), and a new $K_{UF}$ is computed using the actual UFR and TMP values (UFR$_{act}$ and TMP$_{act}$, respectively, in FIG. 9). Then, the needed TMP is re-calculated using Eq. 7, and controller 80 and valve 74 adjust TMP to the new value.

After the initial measurement and calculation of the $K_{UF}$ (during "dialyzer characterization") and the second measurement at or near $\overline{UFR}_{adj}$, $K_{UF}$ is measured, and needed TMP is calculated, approximately hourly during the remainder of the dialysis session. Thus, the system does not merely predict removal of fluid from the patient, it actually controls the ultrafiltration rate so that the target fluid loss is achieved. Moreover, the periodic measurements and adjustments take into account temporal physical changes in the UFR/TMP relationship of dialyzer 12 owing to, e.g., loss of active surface area of the membrane resulting from clotting.

As is seen from equation 8, the fluid removed so far, UF$_t$, is, for time periods up to time t, the sum of the products of measured UFR times the period of time ($\Delta t$) the dialyzer was operating at that UFR.

$$UF_t = \sum_{t=0}^{t} UFR \times \Delta t \qquad (8)$$

During the dialysis session in the automatic control mode, displays 152 and 154, are continuously updated, indicating to the user UF$_t$ and the time remaining, respectively. The numbers displayed in display 152 increase, and the numbers displayed in display 154 decrease. During a session, the operator can adjust the rate of ultrafiltration and/or the time remaining by adjusting knob 150 and/or knob 148. When either knob is adjusted, the appropriate displays will immediately reflect the new operating values and the revised target fluid loss. Further, when the UFR knob 150 is changed, the necessary TMP will be changed immediately. If the UFR knob is changed upward by more than 0.05 kg/hr, and TMP prior to the change was less than 100 mm Hg, then the machine will re-check the operating point within about 7 minutes. This is done to make sure that the machine accurately went to the new operating value. (This sequence is not shown on FIG. 9.)

Controller 80 also includes means to provide warnings to indicate when the desired UFR results in a TMP which is higher or lower than the range of values which can be achieved by system 10. For example, if the $K_{UF}$ for dialyzer 12 is low, and the corresponding $\overline{UFR}$ and TMP necessary to achieve the desired amount of liquid removal are higher than can be achieved by the system, a "high" warning light activates to indicate that either the time will have to be increased or the amount of liquid removal be decreased, to bring the $\overline{UFR}$ to an achievable level. If the $K_{UF}$ for dialyzer 12 is high, and the corresponding $\overline{UFR}$ and TMP necessary to achieve the desired amount of liquid removal are lower than can be achieved by the system, a "low" warning light activates to indicate that either the time will have to be decreased or the amount of liquid removal increased, to bring the $\overline{UFR}$ to an achievable level. A lower limit of TMP of 50 mm Hg is picked for safety reasons, because below this level, there may be sites within dialyzer 12 where, locally, P$_d$ exceeds P$_b$. In such a case, were a leak in the dialyzer membrane to occur, non-sterile dialysate could be infused into the patient's blood.

Cleaning, Disinfecting, and Rinsing Cycles Subsystem

After a dialysis session, the hydraulic pathway of system 10 may be rinsed, cleaned with bleach (sodium hypochlorite solution), or disinfected with formaldehyde. The user may choose which of these cycles to use. Once a rinse, cleaning, or disinfecting cycle is entered by meeting the necessary entrance conditions (described below), the cycle will proceed automatically at the direction of controller 80. At various stages in each cycle, appropriate indicators on the machine (not shown) inform the user of the event taking place.

Referring to FIGS. 7 and 10–12, first, dialyzer 12 is disconnected, lines 50, 55 are connected to inter-connected bypass ports 108, 110, the source of concentrated dialysate solution 18 is disconnected, and hose 41 is connected to rinse port 21. Under these conditions, and assuming the machine blood pump (not shown) is turned off, the controller 80 senses the appropriate conditions for rinsing via proximity switches 120, 122 through signal paths 126, 128 and the blood-pump-off condition via path 142, and enters the rinse cycle. In this cycle pumps 40 (within hydraulic pathway 132), 42, 76 run, and valve 48 (within hydraulic pathway 132) is forced to the dialyzing position shown in FIG. 1, allowing a rinse of water to be flushed through the hydraulic circuitry for water, concentrated dialysate solution, and dialysate. When hose 41 is removed from port 21, the rinsing automatically stops.

If the machine is to be cleaned with bleach, it is first necessary to enter the rinse mode as described above. Then, connector 90, attached to a bottle (not shown) of bleach, is inserted into chemical intake port 102 and keyhole 98, thereby activating a chemical-intake memory (described below) and chemical intake pump 104, causing the machine to draw in bleach at the correct ratio of bleach to flowing water for 10 minutes. After 10 minutes has elapsed, pump 104 turns in the opposite direction for about 5 seconds in order to rinse the chemical intake line 106 with water, and then stops. This returns the machine to the rinse mode, which must persist for 5 minutes. At the end of the 5 minute rinse, the chemical memory is de-activated and the user is notified by a display (not shown) on the front panel that the bleaching cycle is complete and rinsing will continue indefinitely until the operator commands the machine to do something else.

If the machine is to be disinfected with formaldehyde, it is first necessary to enter the rinse mode as described above, but it is not necessary to have cleaned the machine with bleach. Connector 88, attached to a bottle (not shown) of formaldehyde disinfectant, is then inserted into port 102 and keyhole 96, thereby activating the chemical-intake memory and chemical intake pump 104, causing the machine to draw in formaldehyde at the correct ratio to flowing water for 2½ minutes. At the end of the formaldehyde intake interval, all pumps are stopped and water inlet valve 17 is closed, thereby trapping the diluted formaldehyde solution in the hydraulic pathway. The user then turns off the machine and allows the machine to soak with disinfectant solution inside for 2 hours to 4 days. When the machine is turned back on, it immediately commences to rinse for ten minutes. At the beginning of this rinse interval, pump 104 turns in direction opposite to intake for a few seconds, to purge line 106 of concentrated disinfectant. At the conclusion of the 10-minute rinse, the chemical memory is de-activated and the user is informed (by a display—not shown—on the front panel) that the disinfecting cycle is complete, and rinsing continues indefinitely until the operator commands the machine to do something else.

The chemical memory is battery-powered and is set upon activating chemical pump 104. Once the memory is set, a rinse cycle must be completed before dialysis can be resumed by connecting a dialyzer to lines 50, 55 and activating the blood pump; otherwise an alarm will sound, even if the machine is turned off during the chemical pumping. The use of the different keys and keyholes indicates to controller 80 whether a bleach or formaldehyde cycle should begin, and the use of color-coded connections simplifies operator usage.

Other embodiments of the invention are within the following claims.

OTHER EMBODIMENTS

In place of the bleach and formaldehyde treatment liquids, other chemicals may be used.

OTHER INVENTIONS

Subject matter related to the deaeration subsystem was the invention of Steven H. Johnson, whose U.S. patent application entitled "Deaerating Liquid" is being filed simultaneously with the present application, Ser. No. 258,423, now U.S. Pat. No. 4,371,385.

Subject matter related to controlling the transmembrane pressure in the fluid flow transfer device was the joint invention of Steven H. Johnson and Thomas M. Laule, whose U.S. patent application Ser. No. 258,365 entitled "Transmembrane Pressure Control" is being filed simultaneously with the present application.

Subject matter related to the structure of the variable restriction valve was the invention of Thomas M. Laule, whose U.S. patent application Ser. No. 258,366 entitled "Variable Restriction Valve" is being filed simultaneously with the present application.

Subject matter related to the system for sonically measuring ultrafiltrate as it collects in a tube was the joint invention of Steven H. Johnson, Thomas P. Grover and Richard M. Kenshalo, whose U.S. patent application Ser. No. 258,381 entitled "Measuring Low Flowrates" is being filed simultaneously with the present application.

Subject matter related to the automatic control system that achieves a desired amount of ultrafiltration was the joint invention of Terry D. Boucher, Dennis J. Hlavinka, Richard M. Kenshalo, and Steven H. Johnson, whose U.S. patent application Ser. No. 258,379, now U.S. Pat. No. 4,381,999, entitled "Automatic Ultrafiltration Control System" is being filed simultaneously with the present application.

Subject matter related to using a memory in rinsing, cleaning and disinfecting the apparatus was the joint invention of Dennis J. Hlavinka and Thomas P. Grover, whose U.S. patent application Ser. No. 258,380 entitled "Rinsing, Cleaning and Disinfecting Dialysate Preparation and Supply Apparatus" is being filed simultaneously with the present application.

What is claimed is:

1. Dialysate preparation and supply apparatus having a water intake port, a concentrated dialysate solution intake connector, dialysate connectors for delivering fresh dialysate to and removing spent dialysate from a dialyzer, and system pumps for pumping liquids through hydraulic circuitry connected to said intake ports, said hydraulic circuitry including said dialysate connectors, said apparatus further comprising a cleaning and/or disinfecting system comprising
   a chemical intake port on an accessible exterior surface of said apparatus for connection to sources of different treatment liquids, one at a time,
   said port being connected to said hydraulic circuitry, means for regulating the flow of liquid from said chemical port into said hydraulic circuitry, means for providing a plurality of keyholes corresponding to said different treatment liquids in said exterior surface at different locations, each said keyhole being adapted to receive a corresponding key on a treatment liquid connector connected to a source of one said treatment liquid, each said keyhole being adapted to not receive any key corresponding to any other said treatment liquid, means associated with said keyholes for sending electrical signals indicating the presence of a said key in a corresponding said keyhole, and electrical control means for controlling said pumps and said means for regulating, to pump one of said different treatment liquids for a specific period of time and at a specific flowrate depending on which keyhole has a key in it.

2. The system of claim 1 further comprising a water valve between said water intake port and said hydraulic circuitry, and wherein said electrical control means is adapted to cause, upon receiving electrical signals indicating connection of one said treatment liquid, said chemical pump to pump said treatment liquid into said hydraulic circuitry for a period of time long enough to allow said hydraulic circuitry to be filled with diluted treatment fluid and then close said water valve and deactivate said system and chemical pumps to allow said hydraulic circuitry to soak with said treatment liquid.

3. The system of claim 1 wherein said one treatment liquid is bleach.

4. The system of claim 2 wherein said one treatment liquid is disinfectant.

5. The system of claim 4 wherein said disinfectant is formaldehyde.

6. The system of claim 1, 2, 3 or 4 wherein each said key is a different color, and each said means for providing keyholes is of the same color as its corresponding key.

* * * * *